United States Patent [19]

Hirsch et al.

[11] Patent Number: 4,609,666
[45] Date of Patent: Sep. 2, 1986

[54] AROMATASE INHIBITING DERIVATIVES OF α,α-BIS(4-HALOPHENYL)METHYLTETRAZOLES AND TRIAZOLES

[75] Inventors: Kenneth S. Hirsch, New Palestine; Charles D. Jones; Harold M. Taylor, both of Indianapolis, all of Ind.

[73] Assignee: Eli Lilly and Company, Indianapolis, Ind.

[21] Appl. No.: 621,598

[22] Filed: Jun. 18, 1984

[51] Int. Cl.$^4$ ............... A61K 31/41; C07D 249/04; C07D 249/08; C07D 257/04
[52] U.S. Cl. ............... 514/359; 514/381; 514/383; 548/250; 548/252; 548/255; 548/262; 548/373; 548/378
[58] Field of Search ............... 548/250, 252, 254, 255, 548/262; 424/263, 269; 514/381, 383, 359

[56] References Cited

U.S. PATENT DOCUMENTS

| | | | |
|---|---|---|---|
| 3,123,615 | 3/1964 | Rorig | 548/252 |
| 3,155,666 | 11/1964 | Cusic | 548/254 |
| 3,709,901 | 1/1973 | Draber et al. | 548/336 |
| 3,764,690 | 10/1973 | Draber et al. | 548/336 |
| 3,794,653 | 2/1974 | Draber et al. | 548/336 |
| 3,852,056 | 12/1974 | Draber et al. | 71/76 |
| 3,897,438 | 7/1975 | Draber et al. | 548/336 |
| 4,235,893 | 11/1980 | Brodie et al. | 260/397.4 |

FOREIGN PATENT DOCUMENTS 3129193  2/1983  Fed. Rep. of Germany ...... 548/255

OTHER PUBLICATIONS

Siiteri et al., *Handbook of Physiology-Endocrinology II*, Part 1, pp. 615-629 (1977).
Goodman and Gilman's *The Pharmacological Basis of Therapeutics*, 6th Edit., p. 1304 (1980).
Harris, Expl. Cell Biol., 53, pp. 1-8, (1985).
Brodie et al., Endocrinology, 100, pp. 1684-1695 (1977).
Coombes et al., Lancet, pp. 1237-1239 (Dec. 1, 1984).
Santen et al., Ann. Int. Med., 96, pp. 94-101 (1982).
Barone et al., J. Clin. Endocrin. and Metabol., 49(5), pp. 672-676 (1979).
Berkowitz et al., Amer. J. Epid., 121(2), pp. 238-245 (1985).
Tseng et al., J. Clin. Endocrin. and Metabol., 55(5), pp. 1029-1031 (1982).
Zaugg, et al., "Reactions of Some Ester Alkaloids . . . ", *J. Org. Chem.*, 23, 847 (1958).
Balieu, et al., "Tetrazole Analogues . . . ", *Acta Chemica Scandinavica*, 26, 2951 (1972).
Fisher et al., "5-Aroyltetrazoles", *J. Org. Chem.*, 24, 1650 (1959).
Burgess, et al., "Synthesis and Photochemical Decomposition . . . ", *J. Org. Chem.*, 39(7), 940 (1974).
Adelstein, "Antiarrhythmic Agents . . . ", *J. Med. Chem.*, 16(4), 309 (1973).
Chemical Abstract 89:179927v (1978).
Balieu, et al., "Tetrazole Analogues . . . II", *Acta Chemica Scandinavica*, 27, 1233 (1973).
Tolf et al., *Acta Chem. Scand. B.*, 36, 101 (1982).
Chemical Abstracts 89:179908q (1978).
Chemical Abstracts 94:30306n (1981).
Kurihara et al., *Chem. Pharm. Bull.*, 26 (4), 1141 (1978).
Fischer et al., *Helv. Chim. Acta* 63 (6), 1719 (1980).
Chemical Abstracts 90:22461m (1979).

*Primary Examiner*—Richard A. Schwartz
*Assistant Examiner*—Kurt G. Briscoe
*Attorney, Agent, or Firm*—Robert A. Conrad; Leroy Whitaker

[57] ABSTRACT

This invention provides certain azole derivatives, their pharmaceutical formulations, and a method of inhibiting aromatase and treating or preventing estrogen-dependent diseases in mammals.

5 Claims, No Drawings

AROMATASE INHIBITING DERIVATIVES OF α,α-BIS(4-HALOPHENYL)METHYLTETRAZOLES AND TRIAZOLES

BACKGROUND OF THE INVENTION

Estrogens are synthesized from androgenic steroids. In the biosynthetic pathway for estrogen formation, aromatization is an essential step. It is generally believed that if the aromatase enzyme could be effectively inhibited, a useful treatment for estrogen dependent disorders could be obtained (see *Cancer Research*, Vol. 42, Suppl. 8:3261s (1982)).

Several estrogen dependent diseases exist which could be treated with aromatase inhibitors. These include breast cancer, endometriosis, polycystic ovarian disease, benign breast disease, and endometrial cancer. A beneficial effect of antiestrogens in the treatment of breast cancer has been well established (see *Br. J. Cancer*, 25, 270 (1971)). Two of the known aromatase inhibitors, testolactone and aminoglutethimide, have shown a beneficial effect in treatment of breast cancer. See *Cancer Research*, supra.

Endometriosis is characterized by an abnormal proliferation of the endometrium of the uterus. Since the endometrium is dependent on estradiol for its growth, an inhibitor of estrogen production should stop the progression of the disease.

Benign breast disease, or often called fibrocystic breast disease, appears to be dependent on ovarian steroids. See *Cancer*, 49, 2534 (1982). Aromatase inhibitors have not been tried in this disease, but antiestrogens seem to be of benefit. See *Obstet. Gynecol.*, 54, 80 (1979).

Polycystic ovarian disease is one of the most common causes of infertility in women. The disease appears to result from an abnormality in steroid metabolism, and the major form of therapy in this disease is the antiestrogen, clomiphene. See *Clin. Endocrinol.*, 12, 177 (1980).

It is the purpose of this invention to provide certain azole derivatives, their pharmaceutical formulations, and a method for inhibiting the enzyme aromatase in mammals. The invention thus provides for the treatment or prevention of breast cancer and other estrogen-dependent diseases.

SUMMARY OF THE INVENTION

This invention provides a compound of the formula

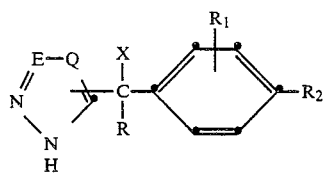

wherein
R is pyridyl or

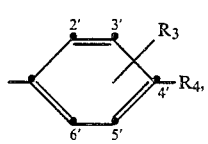

$R_1$, $R_2$, $R_3$, and $R_4$ are independently hydrogen, halo, $C_1$–$C_3$ alkoxy, or trifluoromethyl;

X is hydrogen, hydroxy, methyl, or halo; and
E and Q are independently N or CH, provided that when R is optionally substituted phenyl, $R_1$, $R_2$, $R_3$, and $R_4$ may not all be hydrogen at the same time, or a pharmaceutically acceptable salt thereof.

This invention also provides a method of inhibiting aromatase in mammals which comprises administering an aromatase inhibiting amount of a compound of the above formula. By virtue of their ability to inhibit the enzyme aromatase, the azoles of the above formula are useful in the treatment and prevention of estrogen-dependent diseases, especially breast cancer, in mammals.

A further aspect of this invention is a pharmaceutical formulation comprising one or more of the compounds of the above formula in combination with a suitable pharmaceutical carrier, diluent, or excipient therefor. The formulations provided by this invention are particularly useful in treating mammals suffering from estrogen-dependent diseases such as breast cancer.

DETAILED DESCRIPTION AND PREFERRED EMBODIMENT

The term "halo" refers to fluoro, chloro, bromo, and iodo. The term "$C_1$–$C_3$ alkoxy" refers to methoxy, ethoxy, propoxy and isopropoxy. "Pyridyl" refers to 2-, 4-, or especially 3-pyridyl.

A preferred group of compounds useful in this invention are those wherein:

(a) $R_2$ is halo, especially fluoro or chloro, or trifluoromethyl, (b) X is hydroxy or hydrogen, and (c) R is phenyl ($R_3$ and $R_4$ are both hydrogen) or substituted phenyl, especially where $R_4$ is halo, especially chloro or fluoro, or trifluoromethyl.

Especially preferred compounds are those wherein X is hydrogen or hydroxy, E and Q are each CH, and (a) $R_1$ and $R_2$ are both chloro, especially 3,4-dichloro, and R is unsubstituted phenyl, or (b) $R_2$ is chloro or fluoro, $R_2$ is hydrogen, and R is mono-substituted phenyl, especially where $R_4$ is chloro or fluoro, and $R_3$ is hydrogen.

The most preferred compounds used in this invention are α,α-bis(4-chlorophenyl)-1H-pyrazole-3-methanol, 3-[bis(4-chlorophenyl)methyl]-1H-pyrazole, and α,α-bis(4-chlorophenyl)-1H-pyrazole-4-methanol, and pharmaceutically acceptable salts thereof.

The compounds of this invention can be prepared by any of several methods known in the art. For example, the carbinols of formula I (X=hydroxy) may be prepared by treating a carboxylic ester derivative with the appropriate aryl lithium reagent as summarized by the following scheme:

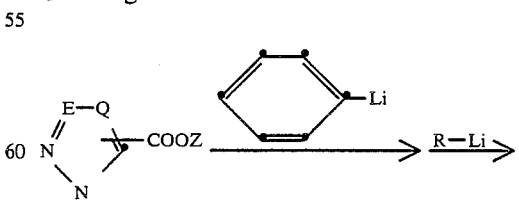

I (X = OH)

wherein Z is, for instance, $C_1$–$C_3$ alkyl. This chemistry is summarized by Burgess and Sanchez, *J. Org. Chem.*, 39 (7), 940 (1974).

A related synthesis described by Fisher et al., *J. Org. Chem.*, 24, 1650 (1959) consists of reacting the appropriate Grignard reagent with the appropriate ketone as summarized by the following scheme:

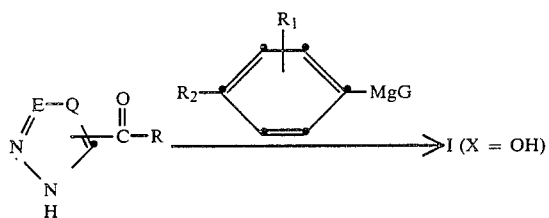

where G is chloro, bromo, or iodo.

A preferred method for preparing certain compounds of this invention consists of the lithiation of a protected azole derivative and the subsequent reaction with a ketone or diaryl methylene compound as summarized in the following scheme:

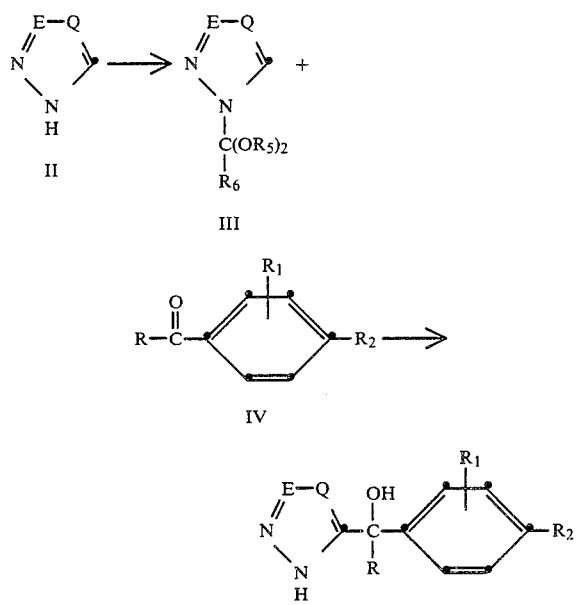

wherein $R_5$ is methyl or ethyl and $R_6$ is hydrogen or methyl. In the above scheme, the azole is heated with a 2-4 fold excess of a trialkyl-orthoformate or -orthoacetate, in the presence of a catalytic amount of an acid, preferably formic acid. The reaction is usually heated from about 60° C. up to the reflux temperature of the reagent and the methanol or ethanol by-product is allowed to distill out of the reaction mixture. The resulting product III is typically distilled by vacuum distillation and used in the reaction with ketone IV. In the latter reaction, intermediate III is treated with a strong base, preferably n-butyllithium, in a non-reactive solvent, such as ether or tetrahydrofuran, to form the corresponding lithium derivative of III. This reaction is generally carried out at low temperatures such as −80° to −40° C. Compound IV is then added to the reaction mixture and stirred for 2-24 hours at temperatures from about −40° to about 30° C. to provide the corresponding carbinol (X=OH) derivative of formula I.

The carbinol derivatives as prepared above are not only useful as aromatase inhibitors but are also useful in preparing other compounds of formula I. Such transformations are known in the art, for instance, those taught in U.S. Pat. No. 3,868,244. For example, the carbinol derivative of formula I (X=OH) can be transformed into the corresponding compound wherein X is hydrogen by heating with a mixture of glacial acetic acid and aqueous hydriodic acid, trifluoroacetic acid and triethylsilane, or similar reagents. The corresponding halo derivatives (X=halo) are prepared from the carbinol compounds by treatment with a suitable halogenating reagent, such as a thionyl halide. A compound of this invention wherein X is methyl can be prepared from the corresponding compounds where X is hydrogen by alkylation with a methyl halide following the general liquid ammonia/alkali metal amide procedure as described in U.S. Pat. No. 2,727,895.

Other methods of preparing the compounds of this invention are known in the art. For example, when the compounds of Formula I are 4-pyrazole derivatives, they may be prepared from the corresponding 5-pyrimidine compounds which are known in the art by first forming a methiodide salt of the pyrimidine compound and then treating the salt with hydrazine. Generally, the reaction is complete within about two to six hours at temperatures of about 50° C. up to the reflux temperature of the reaction mixture. The reaction is preferably carried out in the presence of a non-reactive solvent, such as ethanol.

An alternative method of preparing the compounds of Formula I consists of synthesizing the azole ring as the last step in the synthetic sequence. This method is particularly useful in preparing the pyrazole compounds of this invention, especially the 4-pyrazoles. For example, the reaction of an appropriately substituted malonaldehyde or a derivative thereof, with hydrazine, preferably in the presence of a non-reactive solvent such as an alcohol, provides good yields of the corresponding 4-pyrazole derivative of Formula I. Other such reactions are apparent from the literature.

Intermediate compounds II, IV, and other intermediates required by the above syntheses are commercially available, are known in the art or can be prepared by methods known in the art.

As will be recognized by those skilled in the art, the compounds of the above formula may contain an asymmetric carbon atom. This invention is not limited to any particular isomer but includes the individual enantiomers as well as the racemates of the compounds.

In addition, the azole ring as drawn in the formula represents only one of two or more tautomers possible depending upon how many nitrogen atoms are present in the azole ring. This invention is not limited to any particular tautomeric form but includes all possible tautomeric structures and mixtures thereof. The azole is linked to the rest of the molecule through any carbon atom in the azole ring.

The pharmaceutically acceptable acid addition salts of the bases represented by the above formula can be prepared employing those acids of sufficient acidity to form acid addition salts. These include both inorganic and organic acids such as hydrochloric, hydrobromic, hydriodic, sulfuric, phosphoric, oxalic, methanesulfonic, benzenesulfonic, p-toluenesulfonic, maleic, and the like acids. Preferred acids for salt formation are the inorganic acids, especially hydrochloric acid.

In order to more fully illustrate the preparation of the compounds of this invention, the following examples are provided. The examples are illustrative only and are not intended to limit the scope of the invention in any way.

EXAMPLE 1

α,α-Bis(4-chlorophenyl)-1H-pyrazole-3-methanol

A mixture of 27.2 g of pyrazole, 175 ml of trimethylorthoformate, and 1 ml of 98% formic acid was heated overnight at 100° C. allowing the resulting methanol to distill off. The following day, the temperature was increased to 140° C. and most of the trimethylorthoformate was allowed to distill out. The resulting liquid, approximately one-half of the original volume of the reaction, was treated with 2 g of sodium carbonate and the mixture was vacuum distilled. The fraction which distilled at 68°–70° C./10 torr was collected and weighed 44.85 g. Physical chemistry identified the product as the desired 1-(dimethoxymethyl)pyrazole.

A solution of 14.2 g of 1-(dimethoxymethyl)-pyrazole in 125 ml of tetrahydrofuran at −40° C. was treated with 79 ml of a 1.27M solution of n-butyllithium in hexane under a nitrogen atmosphere. When this addition was complete, 25.2 g of 4,4′-dichlorobenzophenone were added. The reaction was stirred for 48 hours allowing the temperature to come to room temperature. The reaction mixture was added to 200 ml of water and the mixture was extracted with ethyl acetate. The extract was washed with water, dried over magnesium sulfate, filtered and evaporated. The semi-solid residue was triturated with toluene. The toluene filtrate was collected and evaporated and the residue therefrom was purified by high pressure liquid chromatography over silica gel. The appropriate fractions were combined and evaporated to provide 9.5 g of the desired title product. Crystallization from 15% ethyl acetate in hexane provided material with a melting point of 138°–140° C. A second recrystallization provided material with the following analysis.

Analysis for $C_{16}H_{12}Cl_2N_2O$: Calculated: C, 60.21; H, 3.79; N, 8.78; Found: C, 60.39; H, 3.81; N, 8.54.

EXAMPLE 2

3-[Bis(4-chlorophenyl)methyl]-1H-pyrazole hydrochloride

A solution of 0.638 g of α,α-bis(4-chlorophenyl)-1H-pyrazole-3-methanol in 15 ml of trifluoroacetic acid was cooled to 0° C. Under a nitrogen atmosphere, 0.464 g of triethylsilane in 1 ml of methylene chloride was added. After stirring for 1 hour at 0° C., the mixture was poured into water, treated with sodium bicarbonate, and extracted with ethyl acetate. The ethyl acetate extract was dried, filtered, and evaporated to provide 428 mg of the title product (base) as a colorless oil. The residue was dissolved in ether, dry hydrogen chloride was added, and the title product was recovered by filtration providing white crystals with a melting point of 155°–165° C.

Analysis for $C_{16}H_{12}Cl_2N_2.HCl$: Calculated: C, 56.58; H, 3.86; N, 8.25; Cl, 31.31; Found: C, 56.73; H, 3.80; N, 8.08; Cl, 31.26.

EXAMPLE 3

α,α-Bis(4-chlorophenyl)-4H-1,2,4-triazole-3-methanol

Following the general preparation of Example 1, 27.6 g of 1,2,4-triazole, 184 ml of triethylorthoacetate, and 1 ml of 98% formic acid were heated at 100° C. overnight. Distillation provided 48 g of the desired 1-(1,1-diethoxyethyl)-1,2,4-triazole, boiling point 94°–97° C./9 torr.

A solution of 9.25 g of 1-(1,1-diethoxyethyl)-1,2,4-triazole in 150 ml of ether was treated first with 38.5 ml of 1.3M n-butyllithium in hexane and then with 12.6 g of 4,4′-dichlorobenzophenone in the same manner as Exaample 1. The mixture was added to ice and hydrochloric acid producing a white suspension which was recovered by filtration. The solid was recrystallized from 600 ml of methanol/200 ml of water to provide 11.52 g of the desired title product, m.p. 233°–234° C.

Analysis for $C_{15}H_{11}Cl_2N_3O$: Calculated: C, 56.27; H, 3.46; N, 13.13 Found: C, 56.37; H, 3.48; N, 12.86.

EXAMPLE 4

α,α-Bis(4-chlorophenyl)-H-1,2,3-triazole-4-methanol

Following the general procedure of Example 3, 28.8 g of triethylorthoacetate, 4.9 g of 1,2,3-triazole, and 0.2 ml of 98% formic acid were allowed to react to provide 7.56 g of a mixture of 1- and 2-(1,1-diethoxyethyl)-1,2,3-triazole, b.p. 82°–85° C./10 torr.

Four grams of this mixture were treated with 14.4 ml of 1.5M n-butyllithium in hexane and 5.29 g of 4,4′-dichlorobenzophenone in the same manner as described in Examples 1 and 3. The reaction was worked up by adding it to cold 1N hydrochloric acid, extracting with ether, and sequentially washing the ether extract with 1N hydrochloric acid, water, and an aqueous sodium bicarbonate solution. The extract was dried over potassium carbonate, filtered and evaporated. The resulting residue was heated with 25 ml of toluene and filtered. The filtrate, upon cooling, provided 1.12 g of the desired title product. Recrystallization from ethyl acetate/hexane provided α,α-bis(4-chlorophenyl)-1H,1,2,3-triazole-4-methanol with a melting point of 203°–204° C.

Analysis for $C_{15}H_{11}Cl_2N_3O$: Calculated: C, 56.27; H, 3.46; N, 13.12; Found: C, 56.05; H, 3.56; N, 12.91.

EXAMPLE 5

4-[(2,4-Dichlorophenyl)phenylmethyl]-1H-pyrazole

Two grams of [(2,4-dichlorophenyl)phenylmethyl]-malonaldehyde in 10 ml of ethanol were heated with 3 ml of anhydrous hydrazine on a steam bath for two hours. The reaction mixture was poured into water and extracted with ether. The ether extract was dried, filtered, and evaporated. The residue was crystallized twice from Skelley B/acetone to provide 1.2 g of the desired title product, m.p. 131° C.

Analysis for $C_{16}H_{12}Cl_2N_2$: Calculated: C, 63.38; H, 3.99; N, 9.24; Found: C, 63.60; H, 4.13; N, 9.21.

EXAMPLE 6

α,α-Bis(4-chlorophenyl)-1H-pyrazole-4-methanol

The methiodide salt of α,α-bis(4-chlorophenyl)-pyrimidine-5-methanol (12.8 g) was heated to reflux with 3 g of anhydrous hydrazine in ethanol. The original slurry went into solution and then a precipitate formed, at which time 25 ml of water were added. The mixture was heated at reflux for 20 minutes, filtered hot, water was added and the mixture was extracted with ether. The ether was evaporated and the residue was crystallized from chloroform to provide the title product, m.p. 135°–137° C. The NMR and mass spectra were consistent with the desired structure.

The compounds of this invention are useful in preventing or therapeutically treating estrogen-dependent diseases, including breast cancer, in mammals by virtue of their ability to inhibit the enzyme aromatase. The ability to inhibit aromatase was demonstrated by employing a modification of the isolated rat ovarian microsome method of Brodie et al. in *J. Steroid Biochem.*, 7, 787 (1976). In this test system, ovarian microsomes are obtained from rats treated with pregnant mares serum gonadotropin. Test compounds are added to reaction vials containing 0.1 μM 4-androstene-3,17-dione, 100,000 dpm 1,2[$^3$H]-androstenedione, the microsomes and a NADPH generating system. The concentrations of the inhibitors tested ranged between 0.005 and 10 μM. In this assay, aromatization of androstenedione results in the production of [$^3$H]-H$_2$O which is isolated by extracting the samples with chloroform and treating the aqueous phase with charcoal to remove the free steroid. Samples are counted in a liquid scintillation spectrometer and the percent inhibition determined by comparing the results with control samples incubated without inhibitor. Potency is determined based on the concentration of inhibitor in μM required to produce a 50% inhibition of enzyme activity (EC$_{50}$) when the concentration of substrate (androstenedione) is 0.1 μM. The EC$_{50}$'s of certain of the compounds of formula I are summarized in Table 1.

TABLE 1

| Aromatase Inhibition in the Rat Ovarian Microsome Assay | |
|---|---|
| Compound of Formula I | EC$_{50}$* |
| α,α-bis(4-chlorophenyl)-1H—pyrazole-3-methanol | 0.09 |
| 3-[bis(4-chlorophenyl)methyl]-1H—pyrazole hydrochloride | 0.17 |
| α,α-bis(4-chlorophenyl)-4H—1,2,4-triazole-3-methanol | >5.0 |
| α,α-bis(4-chlorophenyl)-1H—1,2,3-triazole-4-methanol | 2.0 |
| 4-[(2,4-dichlorophenyl)phenylmethyl]-1H—pyrazole | 0.31 |
| α,α-bis(4-chlorophenyl)-1H—pyrazole-4-methanol | 0.03 |

*Concentration of compound in μM required to achieve 50% inhibition of aromatase activity when substrate concentration is 0.1 μM.

The compounds may be administered by any number of routes, including the oral, subcutaneous, intramuscular, intravenous, transdermal, and rectal routes. The compounds are usually employed in the form of pharmaceutical compositions. Such compositions are prepared in a manner well known in the pharmaceutical art and comprise at least one active compound of the above formula.

Accordingly, the invention includes a pharmaceutical composition comprising as active ingredient a compound of the above formula associated with a pharmaceutically acceptable carrier. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions of the invention may be formulated so as to provide quick, sustained, or delayed release of the active ingredient after administration to the patient by employing procedures well known in the art.

For oral administration, a compound of this invention can be admixed with carriers and diluents molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The active compounds are effective over a wide dosage range. For example, dosages per day will normally fall within the range of about 0.05 to about 300 mg/kg of body weight. In the treatment of adult humans, the range of about 0.1 to about 50 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

In order to more fully illustrate the operation of this invention, the following formulation examples are provided. The examples are illustrative only and are not intended to limit the scope of the invention. The formulations employ as active compounds any of the pharmaceutical compounds of the above formula.

EXAMPLE 7

Hard gelatin capsules are prepared using the following ingredients:

| | per capsule |
|---|---|
| α,α-bis(4-chlorophenyl)-1H—tetrazole-5-methanol | 250 mg |
| Starch dried | 200 mg |

-continued

| | per capsule |
|---|---|
| Magnesium stearate | 10 mg |
| Total | 460 mg |

The above ingredients are mixed and filled into hard gelatin capsules in 460 mg quantities.

EXAMPLE 8

Capsules each containing 20 mg of medicament are made as follows:

| | per capsule |
|---|---|
| 3-[(4-chlorophenyl)(4-fluoro-phenyl)methyl]-4H—1,2,4-triazole | 20 mg |
| Starch | 89 mg |
| Microcrystalline cellulose | 89 mg |
| Magnesium stearate | 2 mg |
| Total | 200 mg |

The active ingredient, cellulose, starch and magnesium stearate are blended, passed through a No. 45 mesh U.S. sieve and filled into hard gelatin capsules in 200 mg quantities.

EXAMPLE 9

Capsules each containing 100 mg of active ingredient are made as follows:

| | per capsule |
|---|---|
| 4-[bis(4-fluorophenyl)methyl]-1H—1,2,3-triazole | 100 mg |
| Polyoxyethylenesorbitan monooleate | 50 mcg |
| Starch powder | 250 mg |

The above ingredients are thoroughly mixed and are placed in an empty gelatin capsule.

EXAMPLE 10

Tablets each containing 10 mg of active ingredient are made up as follows:

| | per tablet |
|---|---|
| 4-[1-(4-trifluoromethylphenyl)-1-(4-chlorophenyl)ethyl]-1H—pyrazole | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

EXAMPLE 11

A tablet formula is prepared using the ingredients below:

| | per tablet |
|---|---|
| α,α-bis(4-fluorophenyl)-1H—1,2,3-triazole-4-methanol | 250 mg |
| Cellulose microcrystalline | 400 mg |
| Silicon dioxide fumed | 10 mg |
| Stearic acid | 5 mg |
| Total | 665 mg |

The components are blended and compressed to form tablets each weighing 665 mg.

EXAMPLE 12

Suppositories each containing 25 mg of active ingredient are made as follows:

| | per suppository |
|---|---|
| α,α-bis(4-chlorophenyl)-1H—pyrazole-3-methanol | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

EXAMPLE 13

Suspensions each containing 5 mg of medicament per 5 ml dose are made as follows:

| | per 5 ml of suspension |
|---|---|
| 3-[(4-chlorophenyl)(3-pyridyl)methyl]-4H—1,2,4-triazole | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

EXAMPLE 14

An aerosol solution is prepared containing the following components:

| | Weight % |
|---|---|
| α,α-bis(4-chlorophenyl)-4H—1,2,4-triazole-3-methanol | 0.25 |
| Ethanol | 29.75 |
| Propellant 22 (Chlorodifluoromethane) | 70.00 |

The active compound is mixed with ethanol and the mixture added to a portion of the propellant 22, cooled

We claim:

1. A compound of the formula

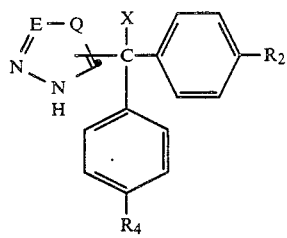

wherein $R_2$ and $R_4$ are independently halo;

X is hydrogen; and

E and Q are independently N or CH, provided that one of E and Q is N and that the

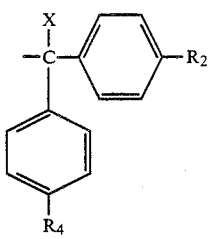

group is attached to one of the carbon atoms of the azole ring, or a pharmaceutically acceptable salt thereof.

2. A pharmaceutical composition useful to treat an estrogen-dependent disease which comprises an effective amount of a compound of the formula

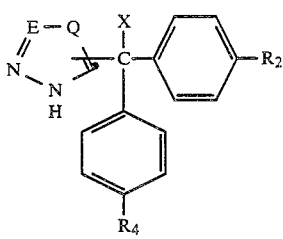

wherein $R_2$ and $R_4$ are independently halo;

X is hydrogen, hydroxy, methyl, or halo; and

E and Q are independently N or CH, provided that one of E and Q is N and that the

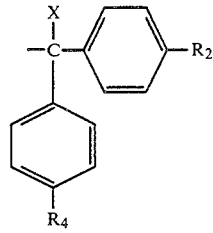

group is attached to one of the carbon atoms of the azole ring, or a pharmaceutically acceptable salt thereof.

3. A method of inhibiting aromatase in a mammal which comprises administrating to said mammal an aromatase inhibiting amount of a compound of the formula

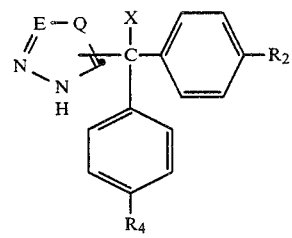

wherein $R_2$ and $R_4$ are independently halo;

X is hydrogen, hydroxy, methyl, or halo; and

E and Q are independently N or CH, provided that one of E and Q is N and that the

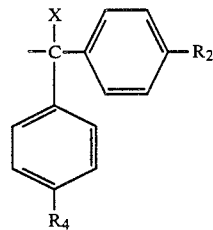

group is attached to one of the carbon atoms of the azole ring, or a pharmaceutically acceptable salt thereof.

4. A method of treating estrogen-dependent disease in a mammal which comprises administering to said mammal an effective amount of a compound of the formula

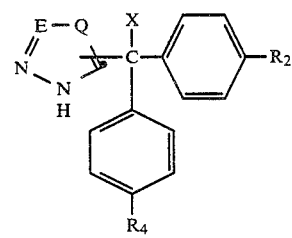

wherein $R_2$ and $R_4$ are independently halo;

X is hydrogen, hydroxy, methyl, or halo; and
E and Q are independently N or CH, provided that
one of E and Q is N and that the
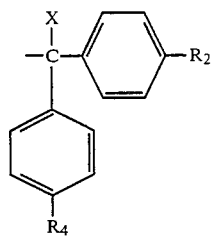
group is attached to one of the carbon atoms of the azole ring, or a pharmaceutically acceptable salt thereof.
5. The method according to claim 4 wherein the estrogen-dependent disease is breast cancer.
* * * * *